United States Patent [19]

Franz et al.

[11] 4,115,095

[45] Sep. 19, 1978

[54] 5-ARYL-1,2,4-THIADIAZOLE-3-CARBOXYLATES AND AGRICULTURAL METHODS

[75] Inventors: John E. Franz, Crestwood; Robert K. Howe, Bridgeton, both of Mo.

[73] Assignee: Monsanto Company, St. Louis, Mo.

[21] Appl. No.: 799,811

[22] Filed: May 23, 1977

[51] Int. Cl.$^2$ .................. A01N 5/00; A01N 9/12; A01N 21/02; C07D 285/10
[52] U.S. Cl. .................. 71/90; 260/302 R; 260/302 D
[58] Field of Search .................. 260/302 D; 71/90

[56] References Cited

PUBLICATIONS

Howe et al., *J. Org. Chem.,* 39(7), 962–964, (1974).

*Primary Examiner*—Alton D. Rollins
*Attorney, Agent, or Firm*—Richard H. Shear; Donald W. Peterson

[57] ABSTRACT

Novel 5-aryl-1,2,4-thiadiazole-3-carboxylates have been found to be effective in reducing herbicidal injury to desirable plants. Said compounds are also useful in increasing the sucrose content of sugar cane.

11 Claims, No Drawings

5-ARYL-1,2,4-THIADIAZOLE-3-CARBOXYLATES AND AGRICULTURAL METHODS

The invention relates to novel 5-aryl-1,2,4-thiadiazole-3-carboxylates that are useful as agricultural chemicals.

One aspect of the present invention encompasses the use of the novel thiadiazole carboxylates to protect desirable plants including crop plants from the phytotoxic action of certain selective pre-emergent herbicides used to control the growth of weeds or other undesirable plants.

A second aspect of the present invention involves the use of said thiadiazole carboxylates to significantly increase the sucrose content of sugar cane.

The novel 5-aryl-1,2,4-thiadiazole-3-carboxylates of the invention have the formula

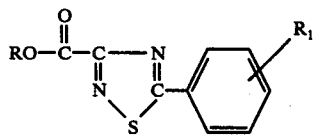

wherein R is hydrogen, lower alkyl or agriculturally acceptable cations; $R_1$ is hydrogen, halogen, trifluoromethyl, cyano, lower alkyl or COOR. Preferably R is lower alkyl and $R_1$ is halogen or cyano.

As used herein, the term "lower alkyl" is meant to include those alkyl groups having from 1 to 5 carbon atoms, inclusive.

The term "agriculturally acceptable cations" is understood to mean those cations which are commonly used in agricultural compositions to form the salt of the free acid, including but not limited to the alkali metal, substituted amine and ammonium cations.

The thiadiazole carboxylates of the foregoing formula may be prepared by cycloaddition of ethoxycarbonylnitrile sulfide to aryl nitriles in accordance with the following reaction scheme:

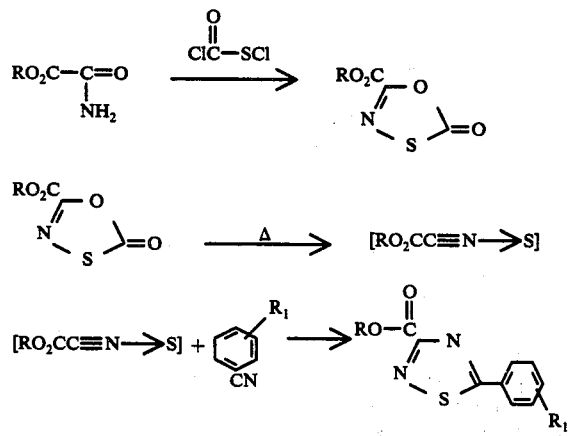

As will be apparent to those skilled in the art, the above reaction scheme illustrates that alkyl oxamate may be reacted with chlorocarbonylsulfenyl chloride to obtain 2-oxo-1,3,4-oxathiazole-5-carboxylic acid ester. Thermolysis of this ester generates an alkoxycarbonylnitrile sulfide which can be converted to the 5-aryl-1,2,4-thiadiazole-3-carboxylate of the foregoing formula by addition thereto of the appropriate benzonitrile.

By way of illustration thereof, the following examples are presented.

EXAMPLE 1

Preparation of Ethyl 2-Oxo-1,3,4-Oxathiazole-5-Carboxylate

A mixture of 99.7 g (0.85 mol) of ethyl oxamate and 552 g (4.23 mol) of chlorocarbonylsulfenyl chloride, prepared in accordance with British Pat. No. 1,079,348, in toluene was held at reflux for 5.25 hours and then was concentrated under vacuum. Benzene was added to the residue, and the solution was extracted twice with water, twice with 5% $NaHCO_3$, again with water, and was dried ($CaSO_4$) and concentrated under vacuum. The residual oil was filtered to remove sulfur and was crystallized twice from methylcyclohexane to give 95.61 g (64%) of white solid, mp 49°–50.5 C.

Anal. Calc'd. for $C_5H_5NO_4S$: C, 34.29; H, 2.88. Found: C, 34.28; H, 2.81.

EXAMPLE 2

Preparation of Ethyl 5-Phenyl-1,2,4-Thiadiazole-3-Carboxylate

A solution of 8.76 g (0.050 mol) of ethyl 2-oxo-1,3,4-oxathiazole-5-carboxylate in 180 g (35 equiv., 1.75 mol) of redistilled benzonitrile was held at reflux for 72 hours. The solution, which contained the product in 62% yield (gc assay), was concentrated under vacuum to 90° C (0.5 torr). The residue was heated with 200 ml of hexane at reflux; the supernatant was decanted, treated with charcoal, filtered, and concentrated under vacuum to 6.1 g of oil and solid. The mixture was chromatographed on 200 g of silica gel (Woelm, for dry column chromatography) with benzene. The first 500 ml of eluate contained 0.8 g of product and impurities. The next 1200 ml of eluate gave 3.82 g (33%) of pure liquid product (gc assay), which crystallized after several months, mp 32°–35° C; $n_D^{25} = 1.5937$; mass spectrum m/e (rel. intensity, fragment) 234 (18, $M^+$), 206 (3, $M^+$-$C_2H_4$), 189 (10, $M^+$-OEt), 135 (100, $M^+$-$EtO_2CCN$), 103 (14, $C_6H_5CN^+$).

Anal. Calc'd. for $C_{11}H_{10}N_2O_2S$: C, 56.40; H, 4.30. Found: C, 56.38; H, 4.40.

EXAMPLE 3

Preparation of Ethyl 5-(p-Chlorophenyl)-1,2,4-Thiadiazole-3-Carboxylate

A sample of p-chlorobenzonitrile was distilled and then crystallized twice from methylcyclohexane to remove impurities that interfered in the following reaction. A solution of 8.76 g (0.050 mol) of ethyl 2-oxo-1,3,4-oxathiazole-5-carboxylate and 68.8 g (0.50 mol, 10 equiv.) of purified p-chlorobenzonitrile was held at 190° C for 72 hours. The solution, which contained the product in 69% yield, was concentrated under vacuum to 150° C (about 2 torr). The residue was crystallized from heptane (charcoal) to give 8.25 g (61%) of gold crystals, mp 98°–99.5° C. A small sample was crystallized twice from heptane (charcoal) to give a white solid, mp 98°–99.5° C.

Anal. Calc'd. for $C_{11}H_9ClN_2O_2S$: C, 49.17; H, 3.38. Found: C, 49.21; H, 3.29.

EXAMPLE 4

Preparation of Ethyl 5-(4-Ethoxycarbonylphenyl)-1,2,4-Thiadiazole-3-Carboxylate

A solution of 1.75 g (0.010 mol) of ethyl 2-oxo-1,3,4-oxathiazole-5-carboxylate and 17.5 g (0.10 mol) of ethyl p-cyanobenzoate was stirred at 190° C for 72 hours, cooled, and dissolved in acetone. Gc analysis of the solution revealed that the product had formed in 53% yield. Concentration of the solution to 90° C (0.1 torr) and two crystallizations of the residue from ethanol (charcoal) at −20° C gave 0.72 g (23.5%) of beige solid, mp 66°–67.5° C.

Anal. Calc'd. for $C_{14}H_{14}N_2O_4S$: C, 54.89; H, 4.61. Found: C, 54.89; H, 4.60

EXAMPLE 5

Preparation of Ethyl 5p-Tolyl-1,2,4-Thiadiazole-3-Carboxylate

A solution of 7.48 g (0.0427 mol) of ethyl 2-oxo-1,3,4-oxathiazole-5-carboxylate and 50.0 g (0.427 mol) of p-tolunitrile (redistilled) was held at 190° C for 72 hours. The reaction mixture, which contained the product in 16% yield, was concentrated under vacuum to 90° C (0.5 torr) to give 4.4 g of black residue. Elution chromatography of this material on 200 g of silica gel (Woelm, for dry column chromatography) with benzene gave 1.7 g of product. Crystallization of this material from hexane (charcoal) gave 0.72 g (7%) of solid, mp 65°–66.5° C.

Anal. Calc'd. for $C_{12}H_{12}N_2O_2S$: C, 58.05; H, 4.87; N, 11.28. Found: C, 58.32; H, 4.91; N, 11.29.

EXAMPLE 6

Similarly, ethyl 5-(p-cyanolphenyl)-1,2,4-thiadiazole-3-carboxylate (mp 172°–173.5° C) may be prepared.

Anal. Calc'd. for $C_{12}H_9N_3O_2S$: C, 55.59; H, 3.50. Found: C, 55.34; H, 3.44.

The free acid may be prepared by hydrolysis of the ester. Salts may be obtained by reacting the free acid with an appropriate base.

As noted above, the thiadiazole carboxylates of the invention may be used to protect desirable plants from the phytotoxic action of certain selective pre-emergent herbicides.

Selective pre-emergent herbicides are those herbicides which will stunt or kill weeds without unduly injuring desirable plants and particularly crop plants. Injury to the desirable plants tends to increase whenever the amount of applied preemergent herbicide is increased to control heavy weed seed infestation or infestation by hard to control weeds. To alleviate injury to desirable plants, the prior art has disclosed the use of various organic compounds designated as safeners, antagonistic agents or antidotes. Regardless of their designation, they all have the common function of reducing or nullifying injury to the desired plants while substantially maintaining herbicidal activity on weeds and other undesired plants. The term "safener" as used hereinafter is intended to be descriptive of the aforesaid function.

Representative of the prior art is U.S. Pat. No. 3,131,509 describing the use of halogenated 2-hydroxyiminoacetanilides for treating seed of crop plants prior to planting to impart resistance to injury by carbamate herbicides, such as 2,3-dichloroallyl N-propylthiolcarbamate, n-propyl N,N-dipropylthiolcarbamate and others.

U.S. Pat. No. 3,719,466 describes treating grain sorghum seed or wheat seed with N,N-diallyl propionamide, N,N-diallylacetamide, 1,8-didecyl naphthalate, 1,8-disodium naphthalate and 1,8-naphthalic anhydride for protection from injury by 2-chloro-2',6'-diethyl-N-(methoxymethyl)acetanilide.

U.S. Pat. No. 3,867,444 describes the use of Schiff's base dichloroacetamides as herbicidal antidotes for the thiocarbmate herbicides, and particularly refers to the thiocarbamates described in U.S. Pat. Nos. 2,913, 327; 3,037,853; 3,175,897; 3,185,720 and 3,198,786. Other patents describing acetanilide herbicides including U.S. Pat. Nos. 2,863,752; 3,442,945; 3,547,620; 3,630,716 and 3,637,847. Of these acetanilides, the most commercially significant are the alphahaloacetanilides.

U.S. Pat. No. 4,003,735 teaches the use as safening agents for selective, pre-emergent acetanilide herbicides of a wide variety of compounds having in common the base structure

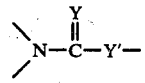

wherein Y and Y' are oxygen or sulfur, such compounds being particularly effective for reducing injury to wheat and sorghum.

It has now been found that the novel 5-aryl-1,2,4-thiadiazole-3-carboxylates of the invention are of value in protecting crop plants, such as rice, sorghum and wheat from the phytotoxic action of acetanilide herbicides. The safeners are especially effective in protecting the crop plant from the phytotoxic action of N-(butoxymethyl)-2-chloro-2', 6'-diethylacetanilide having the common name of butachlor and N-(methoxymethyl)-2-chloro-2', 6'-diethylacetanilide, having the common name of alachlor.

The use of selective herbicides to control the growth of undesired plants is not infrequently accompanied by injury, e.g., malformation, stunting and killing of desirable plants, including the crop plants such as wheat, barley, peas, peanuts, lentils, sugar beets, corn, potatoes, soybeans, cotton, flax, sorghum, and the foliage legumes. The degree of injury to the desirable plants varies with plant species, the herbicide species and the application rates of the herbicide used to control weed growth, particularly when the herbicide is used at high application rates in order to control hard to kill weeds. Injury to the desirable plant species usually results in a loss of crop yield.

As safeners, the 5-aryl-1,2,4-thiadiazole-3-carboxylates of the invention have been found to offer from mild to nearly complete safening action for various corp plants against acetanilide herbicides. They produce little or no injury per se to desirable plants when used at suitable rates of application. On the other hand, these safeners do not cause substantial diminution of herbicidal control over the weeds and other undesirable plant species.

The safeners as used in the practice of this invention can be employed in various ways, including coating of seeds of desirable plant species with the safeners, application to soil prior to or immediately subsequent to the application of the herbicidal agent, or in admixture with the herbicidal agent. Mixtures are particularly preferred inasmuch as they insure the conjoint presence of the safener wherever the herbicidal agent is deposited in or on the soil, as well as reducing expenditure of labor and energy in their application in contrast to separate applications of the herbicide and the safener. The feasibility of making tank mixes of the herbicide and the safener wherein each component would maintain its normal function when applied to the soil was not predictable.

The amount of such safener agents employed in methods and compositions of this invention will vary according to the particular herbicide with which the agent is employed and the rate of application of the herbicide. In each instance, the amount of safening agent employed is a safening effective amount. By a safening effective amount is meant an amount which will cause a reduction of crop injury by the herbicide.

The safening effectiveness of the 5-aryl-1,2,4-thiadiazole-3-carboxylates representative of the foregoing formula with respect to crop plants of rice, sorghum and wheat is demonstrated by the greenhouse test results shown in subsequent Table I wherein for each safening agent, there is shown the percent inhibition of the plants by the herbicide per se, The safening agent per se and the effect of the safening agent in conjunction with the specific herbicide.

In preparation for the tests reported in Table I, a good grade of top soil was placed in a pot and compacted to a depth of 0.9 to 1.2 cm from the top of the pot. A predetermined number of seeds of each of the plant species to be tested were placed on top of the compacted soil. Then a quantity of soil sufficient to substantially fill the pot was measured and placed in a suitable container. A measured quantity of the safening agent dispersed or dissolved in a suitable carrier and a measured quantity of the herbicide dispersed or dissolved in a suitable carrier was thoroughly mixed into the measured quantity of soil which was then deposited over the seeds and leveled.

In Table I, the quantity of herbicide and safening agent is expressed in terms of kilograms per hectare for ease of comparing the greehouse test results with field results. The pots were then placed on a sand bench in the greenhouse and watered from below as needed. The plants were observed at the end of approximately 21 days and the results in terms of percent inhibition of each seed lot were recorded.

The series of tests reported in Table I were conducted over a period of many months during which sunlight exposure and soil, other heat and artificial light conditions in the greenhouse were subject to some variations. In order to provide comparable test conditions, whenever a specific safener was being tested, the designated herbicides were concurrently tested per se. Thus, each test series represents the tests conducted on one or more safeners at the same time and depicts the herbicidal and safening actions under the conditions prevailing at the time the test was conducted.

Table I

| Herbicide | Rate (kg/ha) | Safener | Rate (kg/ha) | Percent Inhibition | | |
|---|---|---|---|---|---|---|
| | | | | Rice | Sorghum | Wheat |
| Alachlor | 2.24 | — | — | 93 | 97 | 58 |
| — | — | Compound 6 | 4.48 | 0 | 0 | 0 |
| Alachlor | 2.24 | Compound 6 | 4.48 | 100 | 65 | 50 |
| — | — | Compound 3 | 8.96 | 0 | 15 | 0 |
| Alachlor | 2.24 | Compound 3 | 8.96 | 100 | 55 | 50 |
| Butachlor | 4.48 | — | — | 70 | 75 | 78 |
| — | — | Compound 6 | 4.48 | 0 | 0 | 0 |
| Butachlor | 4.48 | Compound 6 | 4.48 | 55 | 45 | 35 |

Table I-continued

| Herbicide | Rate (kg/ha) | Safener | Rate (kg/ha) | Percent Inhibition | | |
|---|---|---|---|---|---|---|
| | | | | Rice | Sorghum | Wheat |
| — | — | Compound 3 | 8.96 | 0 | 15 | 0 |
| Butachlor | 4.48 | Compound 3 | 8.96 | 25 | 20 | 15 |
| Alachlor | 0.56 | — | — | 99 | 90 | 75 |
| " | 1.12 | — | — | 100 | 96 | 90 |
| " | 2.24 | — | — | 100 | 96 | 87 |
| " | 4.48 | — | — | 100 | 99 | 96 |
| — | — | Compound 3 | 8.96 | 0 | 0 | 0 |
| Alachlor | 0.56 | Compound 3 | 8.96 | 50 | 20 | 15 |
| " | 1.12 | Compound 3 | 8.96 | 85 | 40 | 50 |
| " | 2.24 | Compound 3 | 8.96 | 90 | 80 | 80 |
| " | 4.48 | Compound 3 | 8.96 | 100 | 80 | 70 |

As illustrated by the above table, the preferred safeners are ethyl 5-(p-chlorophenyl)-1,2,4-thiadiazole-3-carboxylate and ethyl 5-(p-cyanophenyl)-1,2,4-thiadiazole-3-carboxylate.

In accordance with the second aspect of the present invention, the novel 5-aryl-1,2,4-thiadiazole-3-carboxylates have been found to be effective in increasing the sucrose content of sugar cane.

In determining the appropriate rates and time of application to sugar can plants, it is necessary to consider both the chronological age of the plant and its stage of maturity since cane, depending upon the practice in different geographical areas, is grown from 9 to about 30 months before harvest. Application at a rate of from about 0.11 to 5.6 kilograms per hectare can be made from about 2 to 10 weeks prior to the projected harvest date. Preferably, such applications are made from 3 to 7 weeks before said date.

The active ingredients of this invention can be conveniently applied to the plants as an aqueous solution or suspension. For example, a liquid composition may be applied from a boom-spray, or a solid dust composition where the active component is diluted with an inert solid such as clay can be flown on the plants from an aircraft. Suitable liquid compositions include surfactants such as those enumerated in U.S. Pat. Nos. 3,224,865 and 3,245,775. Preferred surface-active agents which are convenient to use in liquid compositions of this invention are of the non-ionic type such as alkylphenoxypoly(ethyleneoxy)ethanols, polyethylene oxide adducts of fatty and resin acids, and long chain alkyl mercaptan adducts with ethylene oxide.

A particularly preferred carrier for the acids or salts of this invention is water with about 0.1 to 2.0% by weight of sufactant added thereto. It has been found convenient to apply the compositions to the plants in the form of aqueous solutions, suspensions or emulsions, the dilution being such that a spray volume of from about 10 to 30 liters of liquid per hectare will contain the desired dosage of active ingredient. It will be recognized, however, that higher or lower total spray volumes can be beneficially employed depending upon the particular dispensing apparatus and other factors well understood by those skilled in the art.

The specific test data which follows are presented as illustrative, non-limiting demonstrations of the useful and unexpected properties of the compounds of this invention.

About 38 mg of Compound 3 is suspended in 0.3 ml of water containing 0.1% Sterox NJ as a surfactant. The resultant solution is then applied to the tip of each of the stalks to be tested with the exception of the untreated controls. Ten of these stalks were harvested 4 weeks after such treatment and ten more were harvested 5 weeks after such treatment.

The top 15 joints of the treated cane as well as those of similar untreated cane are removed, combined and analyzed in terms of juice purity and pol percent cane, following the so-called "press method" developed by T. Tanimoto, Hawaiian Planters Record, 57, 133 (1964). "Pol percent cane" is a polarimetric determination and equals the percentage of sucrose if the latter is the only substance in the solution which will rotate the plane of polarized light. In any event, determination of the pol percent cane is a standard and effective method for determining the sucrose content of sugar cane. The results are given in Table II below.

Table II

|  | FOUR WEEKS | | FIVE WEEKS | |
| --- | --- | --- | --- | --- |
|  | Juice Purity | Pol % Cane | Juice Purity | Pol % Cane |
| Control (untreated) | 79.77 | 9.67 | 81.72 | 11.38 |
| Treated sugar cane | 83.55 | 11.66 | 88.47 | 14.50 |

The treated plants clearly demonstrated a substantial increase in both of the factors measured at both harvest dates.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound having the formula

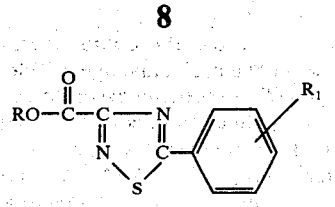

wherein R is hydrogen, lower alkyl or agriculturally acceptable cations; $R_1$ is hydrogen, halogen, trifluoromethyl, cyano, lower alkyl or COOR.

2. A compound according to claim 1 wherein R is lower alkyl.

3. A compound according to claim 2 wherein $R_1$ is cyano or halogen.

4. A compound according to claim 3 which is ethyl 5-(p-chlorophenyl)-1,2,4-thiadiazole-3-carboxylate.

5. A compound according to claim 3 which is ethyl 5-(p-cyanophenyl)-1,2,4-thiadiazole-3-carboxylate.

6. A method for reducing or preventing phytotoxic injury by a pre-emergent acetanilide herbicide to desirable plants or crop plants which comprises applying to the desirable plant or crop seed or to the soil in which the seed is planted, a substantially non-phytotoxic safening amount of a compound having the formula

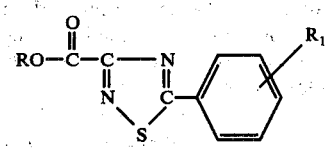

wherein R is hydrogen, lower alkyl or agriculturally acceptable cations; $R_1$ is hydrogen, halogen, trifluoromethyl, cyano, lower alkyl or COOR.

7. A method according to claim 6 wherein R is lower alkyl.

8. A method according to claim 7 wherein $R_1$ is cyano or halogen.

9. A method according to claim 7 wherein said compound is ethyl 5-(p-chlorophenyl)-1,2,4-thiadiazole-3-carboxylate.

10. A method according to claim 7 wherein said compound is ethyl 5-(p-cyanophenyl)-1,2,4-thiadiazole-3-carboxylate.

11. A method according to claim 6 wherein said herbicide is alachlor or butachlor.

* * * * *